United States Patent

Cooper et al.

[11] Patent Number: 5,962,007
[45] Date of Patent: Oct. 5, 1999

[54] USE OF A MULTI-COMPONENT COIL MEDICAL CONSTRUCT

[75] Inventors: Kevin Leonard Cooper, Warren; Shawn Thayer Huxel, Lakehurst; Murty Narayan Vyakarnam, Edison; Arindam Datta, Hillsborough; Jie Jenny Yuan, Bridgewater, all of N.J.

[73] Assignee: Indigo Medical, Inc., Cincinnati, Ohio

[21] Appl. No.: 08/994,898

[22] Filed: Dec. 19, 1997

[51] Int. Cl.[6] ............... A61F 2/06; A61F 2/04; A61M 29/02

[52] U.S. Cl. ............ 424/426; 606/194; 623/1; 623/12

[58] Field of Search ............ 424/426; 623/1, 623/12; 606/194

[56] References Cited

U.S. PATENT DOCUMENTS

| | | | |
|---|---|---|---|
| 5,015,253 | 5/1991 | MacGregor | 623/1 |
| 5,059,211 | 10/1991 | Stack et al. | 606/198 |
| 5,085,629 | 2/1992 | Goldberg et al. | 604/8 |
| 5,147,385 | 9/1992 | Beck et al. | 623/1 |
| 5,160,341 | 11/1992 | Brenneman et al. | 606/198 |
| 5,171,262 | 12/1992 | MacGregor | 623/1 |
| 5,192,289 | 3/1993 | Jessen | 606/155 |
| 5,246,445 | 9/1993 | Yachia et al. | 606/108 |
| 5,292,321 | 3/1994 | Lee | 606/28 |
| 5,419,760 | 5/1995 | Narcisco, Jr. | 604/8 |
| 5,423,885 | 6/1995 | Williams | 623/1 |
| 5,443,458 | 8/1995 | Eury | 604/891.1 |
| 5,500,013 | 3/1996 | Buscemi et al. | 623/1 |
| 5,527,337 | 6/1996 | Stack et al. | 606/198 |
| 5,551,954 | 9/1996 | Buscemi et al. | 623/1 |
| 5,593,434 | 1/1997 | Williams | 623/1 |
| 5,599,291 | 2/1997 | Balbierz et al. | 604/8 |
| 5,618,298 | 4/1997 | Simon | 606/194 |
| 5,626,611 | 5/1997 | Liu et al. | 606/230 |
| 5,670,161 | 9/1997 | Healy et al. | 424/426 |

FOREIGN PATENT DOCUMENTS

| | | |
|---|---|---|
| 0 528 039 A1 | 11/1991 | European Pat. Off. . |
| 0 615 769 A1 | 9/1993 | European Pat. Off. . |
| 0 604 022 A1 | 11/1993 | European Pat. Off. . |
| 0 634 152 A1 | 6/1994 | European Pat. Off. . |
| 0 689 807 A2 | 6/1995 | European Pat. Off. . |
| 0 761 251 A1 | 10/1995 | European Pat. Off. . |
| WO 90/04982 | 5/1990 | WIPO . |
| WO 93/15787 | 8/1993 | WIPO . |
| WO 95/26762 | 10/1995 | WIPO . |

*Primary Examiner*—Carlos A. Azpuru

[57] ABSTRACT

There is described a process for deploying a medical construct in a body cavity, so as to function for example as a stent in a body lumen. The construct is used by forming a coil from a strand that has an interior and an exterior portion, and thereafter heating while expanding the coil so as to melt only the exterior portion. When that melted portion resolidifies with the coil in the expanded state, the coil's integrity and resistance against forces such as compression is maintained by the unmelted but stretched interior portion, and the expanded shape is maintained by the adhesiveness of the solidified exterior portion.

10 Claims, 1 Drawing Sheet

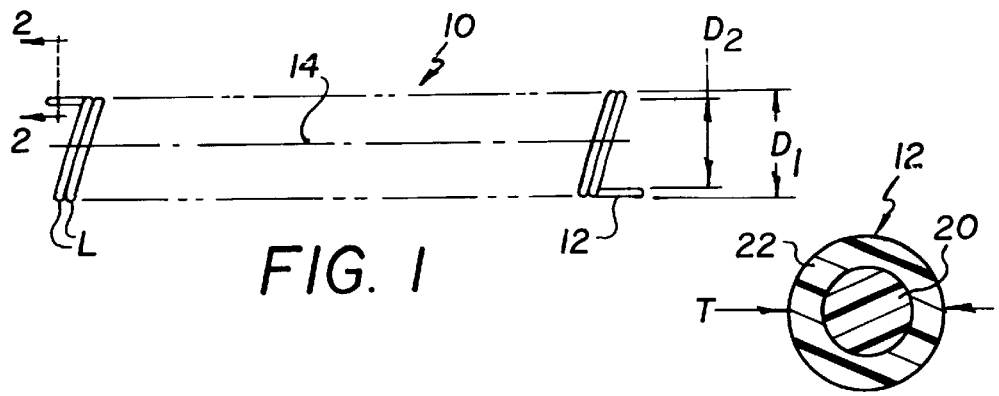
FIG. 1
FIG. 2
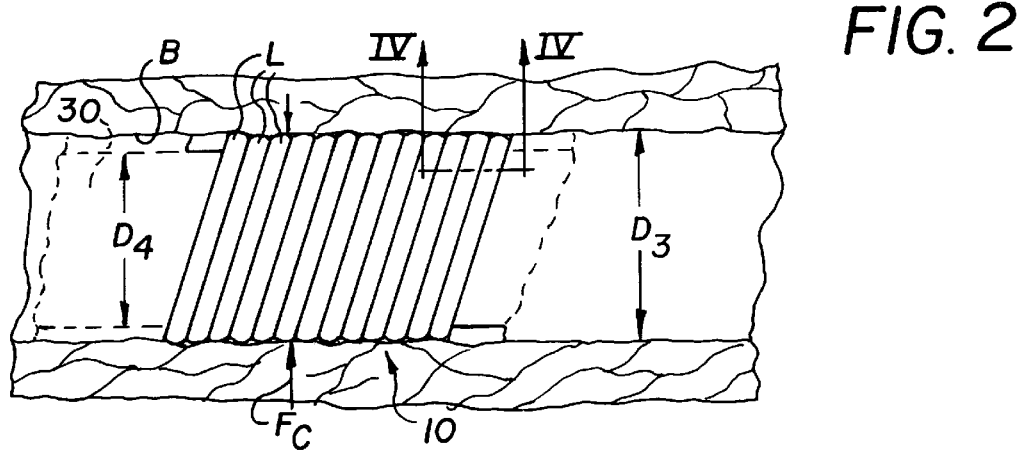
FIG. 3
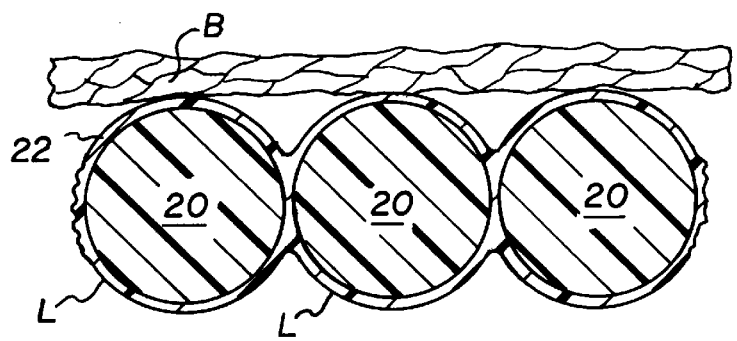
FIG. 4

5,962,007

USE OF A MULTI-COMPONENT COIL MEDICAL CONSTRUCT

FIELD OF THE INVENTION

This invention relates to a method of deploying a stent having interior and exterior portions with different melting temperatures.

BACKGROUND OF THE INVENTION

There has been a need to replace metallic stents with those formed from biodegradable materials. However, any such replacement needs to maintain the advantages of metallic stents, that is, the strength and resistance against compressive forces that tend to reclose the lumen opened by the stent.

It is known to provide biodegradable thermoplastic stents that are deployed by heating the plastic until it softens, and then expanding the softened stent until it achieves a desired diameter, such as that of the body lumen in which it is inserted. For example, U.S. Pat. No. 5,670,161 discusses a tubular stent so processed, as well as (in column 2) prior art tubular stents in Beck et al, U.S. Pat. No. 5,147,385. Particularly as to the latter, it explains that the '385 stent is heated above its melting temperature (the polymer "enters a liquid phase in the [deployment] temperature that Beck discloses"), and hence "improved strength characteristics using the stent described by Beck is limited". The solution of the '161 patent is to use a copolymer of the Beck homopolymer, the copolymer having melting temperatures that greatly exceed the deployment heating temperature so that there is no melting of the copolymer stent.

Thus, the trend as shown by the '161 patent is to avoid melting a tubular thermoplastic stent when it is deployed by heating and expanding it, as this weakens the strength properties of the stent. That is, the entire plastic tube of the '385 patent melts, thus losing its integrity and its inherent strength. However, the "solution" of requiring only the use of a copolymer is one that is undesirable due to the limited ability to resist compressive forces in any new expanded form. There has been a need, therefore, to provide a process of using a thermoplastic stent by heating and expanding, that is not limited just to single materials but which retains the strength properties of, e.g., copolymers.

SUMMARY OF THE INVENTION

We have designed a process which satisfies the above-noted needs. That is, the invention is based upon the realization that it is possible to construct a coil stent from a strand that has an interior and an exterior portion, the two portions having two different melting temperatures and, thereafter, heating while expanding the coil so as to melt only the exterior portion. When that melted portion resolidifies with the coil in the expanded state, the coil's integrity and resistance against forces such as compression is maintained by the unmelted but expanded interior portion, and the expanded shape is maintained by the adhesiveness of the solidified exterior portion.

More specifically, in accord with one aspect of the invention there is provided a method of delivering and deploying a medical construct in a body cavity, comprising the steps of:

a) providing a medical construct comprising a strand wound into a coil, the strand comprising an interior portion that has a melting temperature $T_{m_i}$ and an exterior portion that comprises a biodegradable, biocompatible polymer having a melting temperature $T_{m_e}$, the melting temperatures being greater than body temperatures; the coil having a longitudinal axis and an outside diameter less than that of the body cavity;

b) inserting the medical construct into the body cavity and moving the medical construct to a deployment position within the cavity;

c) deploying the medical construct by heating it to a deployment temperature that exceeds $T_{m_e}$ but not $T_{m_i}$ so as to melt the exterior portion but not the interior, and expanding the outside diameter radially until the diameter approximates the interior diameter of the body cavity; and d) allowing the deployed medical construct to cool while expanded, so that the outer portion that has melted at the deployment temperature, fuses at least a portion of the coil together at the body cavity temperature at the expanded diameter, thereby increasing the coil's resistance to any shear forces applied to the coil parallel to the axis, and to compressive forces applied transversely to the axis.

In accord with another aspect of the invention, there is provided a method of forming a tubular stent in situ in a body lumen, comprising the steps of:

a) inserting into the lumen a construct comprising a coil formed by wrapping a strand about an axis, the coil being narrower in diameter than the inside diameter of the lumen;

b) heating the coil to a temperature sufficient to melt only the outside surface of the strand but not the strand portion inside the surface;

c) expanding the coil while still at the temperature until its diameter approximates that of the lumen; and d) cooling the coil so as to solidify the melted surface portion while the coil is expanded, so that the coil solidifies into a tube.

Accordingly, it is an advantageous feature of the invention that a plastic coil stent can be deployed by expanding it at a temperature that melts outer portions of the stent, without sacrificing and indeed while enhancing mechanical strength properties.

Other advantageous features will become apparent upon reference to the following Detailed Description, when read in light of the attached drawings.

BRIEF DESCRIPTION OF THE DRAWINGS

FIG. 1 is a fragmentary elevational view of an undeployed coil stent prior to its use in the invention;

FIG. 2 is a section view taken along the line II—II of FIG. 1;

FIG. 3 is a fragmentary elevational view of the same stent, following its deployment by expansion while on a balloon catheter inside a body lumen shown in phantom and in section, respectively; and FIG. 4 is a fragmentary section view taken generally along the line IV—IV of FIG. 3.

DETAILED DESCRIPTION OF THE PREFERRED EMBODIMENTS

What follows is a description of the preferred embodiments, wherein a single coil stent is provided comprising certain preferred materials, and is deployed in certain body lumens at certain preferred heating temperatures and pressures while on a preferred deploying instrument, i.e., a balloon catheter. In addition, the invention is applicable regardless of the materials utilized, how it is used in a living body, at what temperatures and pressures it is deployed, and what the deploying instrument is. It is also useful if multiple helix coils are used.

As shown in FIG. 1, the preferred construct for use in this invention is a coil stent 10 formed by winding a strand 12 about an axis 14 so that the coil has an unexpanded outside diameter $D_1$ and an unexpanded inside diameter $D_2$. Each loop "L" of the coil may, or may not, contact the next adjacent loop.

As shown in FIG. 2, strand 12 has a thickness "T" and comprises an interior portion 20 and an exterior portion 22. Preferably, portion 20 is a sheath tightly adhering to the interior portion. Most preferably, both portions are biodegradable, biocompatible materials, and particularly, biodegradable polymers such as polyesters, discussed below.

Preferred examples for $D_1$, $D_2$ and T are as follows:

$D_1$=1 mm to about 50 mm, most preferably about 5 mm to 8 mm for a urethral stent;

$D_2$=0.95 mm to about 48 mm, most preferably about 3 mm to 6 mm for a urethral stent;

T=0.025 mm to 2.0 mm, most preferably about 1 mm for a urethral stent. Other examples are also useful, depending upon where in a living body the stent is to be deployed.

In accordance with one aspect of the invention, portions 20 and 22 are selected so that the melting temperature $T_{m_i}$ of portion 20 greatly exceeds the temperature used to deploy the stent, as well as the melting temperature $T_{m_e}$ of portion 22. Likewise, $T_{m_e}$ is less than the deployment temperature by an amount sufficient to cause at least a portion and preferably all of portion 22 to melt upon deployment.

Thus, in accordance with another aspect of the invention, the method of delivering and deploying the stent 10, as depicted in FIG. 3, comprises wrapping it around a deploying instrument 30, such as a balloon catheter, while the coil still has outside diameter $D_1$. The stent and catheter are then deployed within a living body, preferably within a lumen B, and the catheter is heated to its deployment temperature $T_D$. Thereafter, the catheter is expanded to the diameter $D_4$, FIG. 3, and stent 10 is forced to also expand so that its outer diameter $D_3$ approximates the inside diameter of lumen B. However, because $T_D$ is greater than $T_{m_e}$ and less than $T_{m_i}$, portion 22 of the coil has melted, but not portion 20. By proper selection of a glass transition temperature $T_g$ for portion 20, that portion has softened, preferably. Thereafter, while in the expanded state shown, FIG. 3, the catheter and stent are cooled to body temperature for the lumen, causing portion 22 to solidify, FIG. 4, to fuse the coil with loops L in contact at their expanded outside diameter $D_3$, and an expanded inside diameter $D_4$, FIG. 3.

A preferred temperature for the deployment temperature $T_D$ is from 45° C. to 70° C. Most preferred is 50° C. to 55° C. A preferred pressure for expanding the coil is from 1 Atm to 25 Atm pressure and most preferably, about 1 Atm to 10 Atm.

Following a cooling step, the pressure within catheter 30 is released and the latter allowed to shrink, so that it can be withdrawn from lumen B while leaving stent 10 behind.

Representative examples of useful values of $D_3$ and $D_4$ include, for $D_3$, from about 1.5 mm to about 75 mm, and $D_4$ from about 1.5 mm to about 70 mm, depending in part, of course, on the thickness value of T. When used in a urethra following treatment of benign prostatic hyperplasia, $D_3$ is about 8 to 10 mm and $D_4$ about 6 to 8 mm.

Regarding the materials of portions 20 and 22, most preferably portion 20 comprises a polyester selected from the group consisting of stiff, rigid high $T_g/T_m$ polymers, copolymers and blends of poly(lactide) and poly(glycolide), while portion 22 comprises a polyester selected from soft, flexible, low $T_g/T_m$ polymers, copolymers, and blends of poly(ε-caprolactone), and copolymers and blends of poly(p-dioxanone) and poly(trimethylene carbonate). Highly preferred ratios of comonomers include, e.g., co-glycolide/lactide in ratios of (95:5) to (5:95).

Additionally, either portion 20 or 22 can have co-polymerized therewith, monomers selected from portion 22 or 20, respectively.

Suitable lactone monomers from which such polymers are formed may be selected from the group consisting of glycolide, lactide (1, d, dl, meso), p-dioxanone, delta-valerolactone, beta-butyrolactone, epsilon-decalactone, 2,5-diketomorpholine, pivalolactone, alpha, alpha-diethylpropiolactone, ethylene carbonate, ethylene oxalate, 3-methyl-1, 4-dioxane-2, 5-dione, 3,3-diethyl-1, 4-dioxan-2, 5-dione, gamma-butyrolactone, 1,4dioxepan-2-one, 1,5-dioxepan-2-one, 1,4-dioxan-2-one, 6,8-dioxabicycloctane-7-one and combinations of two or more thereof. Preferred lactone monomers are selected from the group consisting of glycolide, lactide, trimethylene carbonate, ε-caprolactone and p-dioxanone.

Yet another alternative is to select portion 20 from an absorbable glass, non-absorbable polymers or ceramic fibers, or from a metal.

It is also possible to add agents such as barium sulfate to give radio opaqueness, or drugs for site specific delivery.

The above-noted preferred polymers for the interior and exterior portions preferably have the following significant properties, where "$T_g$" is the glass transition temperature and $T_m$ is the melting temperature:

| Polymer | $T_g$(° C.) | $T_m$(° C.) |
|---|---|---|
| poly(lactide) | 65 | 190 |
| poly(glycolide) | 45 | 220 |
| poly(ε-caprolactone) | −60 | 60 |
| poly(p-diaxanone) | −10 | 110 |
| poly(trimethylene carbonate) | −25 | NA |

To allow the interior or exterior polymers to be used as a drug delivery matrix, the polymer can be mixed with a therapeutic agent. The variety of different therapeutic agents which can be used in conjunction with the polymers of the present invention is vast. In general, therapeutic agents which may be administered via the pharmaceutical compositions of the invention include, without limitation: antiinfectives such as antibiotics and antiviral agents; analgesics and analgesic combinations; anorexics, antihelmintics; antiarthritics, antiasthmatic agents; anticonvulsants; antidepressants; antidiuretic agents; antidiarrheals; antihistamines; antiinflammatory agents; antimigrain preparations; antinauseants; antineoplastics; antiparkinsonism drugs, antipruritics; antipsychotics; antipyretics, antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary, peripheral and cerebral; central nervous system stimulants; cough and cold preparations, including decongestants; hormones such as estradiol and other steroids, including corticosteroids; hypnotics; immunosuppressives; muscle relaxants; parasympatholytics; psychostimulants; sedatives; and tranquilizers; and naturally derived or genetically engineered proteins, polysaccharides, glycoproteins, lipoproteins, or thrombogenetic and restenoic reducing agents.

Matrix formulations may be formulated by mixing one or more therapeutic agents with the polymer. The therapeutic agent, may be present as a liquid, a finely divided solid, or any other appropriate physical form. Typically, but optionally, the matrix will include one or more additives, such as diluents, carriers, excipients, stabilizers or the like.

The amount of therapeutic agent will depend on the particular drug being employed and medical condition being treated. Typically, the amount of drug represents about 0.001% to about 70%, more typically about 0.001% to about 50%, most typically about 0.001% to about 20% by weight of the matrix.

The quantity and type of polymer incorporated into the drug delivery matrix will vary depending on the release profile desired and the amount of drug employed. The product may contain blends of polymer to provide the required release profile or consistency to a given formulation.

Upon contact with body fluids, the polymer undergoes gradual degradation (mainly through hydrolysis) or dissolution under physiological conditions with concomitant release of the dispersed drug for a sustained or extended period.

Methods are known for forming a composite polymeric strand of two different polymers, for use herein. E.g., U.S. Pat. No. 5,626,611 teaches a useful method of making a strand used in this invention by co-extruding the interior portion and exterior portion polymers. Alternatively, the interior portion polymer can be extruded and the resulting wire used to wire-coat the exterior portion polymer from a melt.

However the strand is formed, thereafter the strand is wrapped around a mandrel to form the coil shape of the device used in the present invention.

Because the deployment process of the present invention melts only the exterior portion, but not the interior portion, the process of the invention allows the device to conform to the desired shape (e.g., expanded to conform to the lumen of an artery), and still dramatically increase its resistance to compressive and hydrostatic loads. Yet, the device is highly flexible during delivery and deployment, a critical feature when there is a need to pass the stent through small tortuous arteries from a person's extremities.

Thus, the end use of the process is in placing stents, grafts, nerve guides, and anastomosis couplers. The most preferred device is a stent, most preferably a stent for urological applications.

The device of the present invention has the added capability over that of prior art tubular stents of tissue in-growth control, since the level of coil fusion can be governed to provide a tube construct that is perforated and thus, impervious to cell proliferation. That is, the loops of the coil may be spaced apart for the perforated portion, and/or portions of the coil portion 20 can be uncoated with portion 22, leaving gaps in the meltable polymer otherwise used to solidify the looks together. The spacing of the loops, or the gaps in portion 22 are selected to be of sufficient amounts as to create the desired perforations. For some cases, tissue in-growth is imperative since some of the devices of the present invention such as cardiovascular stents and vascular grafts are utilized in the blood stream. Thus, it is advantageous that the device is endothelialized (i.e., perforated for tissue in-growth) to prevent particulates of the device from dislodging from the vessel wall and traveling to other parts of the body.

Conversely, for other uses of the present invention such as urethral stents, it is highly desirable that the device is a solid structure (i.e., completely fused coils as shown in FIG. 3) so that it breaks down and passes through the urethral tract in small particulates to prevent absorption from occurring in the vessel wall. This might be highly desirable for FDA approval, since it is possible for the device to discharge from the body in less than 30 days, eliminating the need for rigorous safety and efficacy studies.

Consequently, the tissue growth control and enhanced rigidity of the process of the present invention allows for a variety of needs to be met for a wide range of medical applications that would not otherwise be abated by the devices of the prior art. For example, there is a great need for such a device in stenting blood vessels or the urethra to open occlusions due to plaque build-up or to maintain patency following surgical procedures for, e.g., benign prostate hypertrophy. A construct, such as that of the present invention, that is flexible (i.e., a coil) during delivery, but rigid after deployment (i.e., a tube) and has the potential for controlled tissue growth, meets the needs for applications as broad in scope as arterial and urethral stents, grafts, and anastomotic couplers.

EXAMPLES

The following examples are illustrative of the principles and practice of this invention, although not limited thereto. Numerous additional embodiments within the scope and spirit of the invention will become apparent to those skilled in the art. The examples are for the in-situ thermally formed coil construct described above.

Example No. 1

A coil stent was prepared from the process described above, with an interior portion 20 of poly(lactide) and the exterior portion 22 of poly(caprolactone). The dimensions, FIGS. 1 and 2, were $D_1$=6 mm, $D_2$=4 mm, and T=1 mm. The diameter of portion 20 was about 0.5 mm.

This coil was placed on a foley balloon catheter having an outside diameter of the same value as $D_2$, and heated to 60° C. Thereafter, it was expanded using a pressure in the catheter of about 5 atmospheres, until diameter $D_3$, FIG. 3, was about 8 mm. The catheter was cooled so that the coil became fused, and the pressure and then the catheter were removed. The coil was found to have resistances to the following compressive load $F_C$, per Mm length, FIG. 3:

$F_C$=2.19 N/mm

By comparison, $F_C$ of this coil prior to expansion and fusion of the coils, was only 0.27 N/mm.

This established that the process of the invention has the dual advantage of deforming and fusing at its surface, which forms a tubular structure with excellent radial stiffness, while not deforming at its core so as to lose its function as a mechanical support to the wall of a body cavity. That is, the stiff interior portion 20 acts to control the rate of uncoiling and provides structural integrity and rigidity to the exterior portion 22 while it is being melted.

The invention disclosed herein may be practiced in the absence of any element which is not specifically disclosed herein.

The invention has been described in detail with particular reference to preferred embodiments thereof, but it will be understood that variations and modifications can be effected within the spirit and scope of the invention.

What is claimed is:

1. A method of delivering and deploying a medical construct in a body cavity, comprising the steps of:

a) providing a medical construct comprising a composite strand wound into a coil, said strand comprising an interior portion that has a melting temperature $T_{m_i}$, and an exterior portion of a material different from that of the interior portion and which comprises a biodegradable, biocompatible polymer having a melting temperature $T_{m_e}$, said melting temperatures being greater than body temperatures; said coil having a longitudinal axis and an outside diameter less than that of the body cavity;

b) inserting the medical construct into the body cavity and moving the medical construct to a deployment position within the cavity;

c) deploying the medical construct by heating it to a deployment temperature that exceeds $T_{m_e}$ but not $T_{m_i}$ so as to melt said exterior portion but not said interior, and expanding said outside diameter radially until said diameter approximates the interior diameter of the body cavity; and d) allowing the deployed medical construct to cool while expanded, so that said exterior portion that has melted at said deployment temperature, fuses at least a portion of the coil together at the body cavity temperature at the expanded diameter, thereby increasing the coil's resistance to any shear forces applied to the coil parallel to said axis, and to compressive forces applied transversely to said axis.

2. A method as defined in claim 1, wherein said entire strand comprises polymeric material, and said interior portion comprises a biodegradable, biocompatible plastic having a glass transition temperature $T_g$ sufficient to allow expansion of said coils while heating at a deployment temperature but which resists bending at normal body cavity temperatures.

3. A method as defined in claim 1, wherein said construct is a stent and said step a) comprises mounting said stent on a balloon catheter;

said step b) comprises inserting the stent and catheter into the body cavity;

said step c) comprises heating and expanding said balloon catheter to heat and expand said coil and melt said exterior portion; and said step d) comprises removal of heat from said balloon catheter by an amount sufficient to cool the expanded stent to the temperature of the body cavity.

4. A method as defined in claim 1 or 3, wherein said deployment temperature is between about 50° C. and 70° C., said $T_{m_i}$ is at least 75° C., said $T_{m_e}$ is a range of temperatures including those less than 50° C., and said $T_g$ is about 65° C.

5. A method as defined in claim 1 or 3, wherein said expanding step comprises applying pressure to the interior of said balloon catheter up to about 25 Atm.

6. A method as defined in claim 1 or 2, wherein said interior portion comprises a polyester selected from the group consisting of poly(lactide), poly(glycolide), and copolymers and blends thereof.

7. A method as defined in claim 6, wherein said exterior portion comprises a polyester selected from the group consisting of poly(lactide), poly(glycolide), poly(ϵ-caprolactone) and copolymers and blends thereof, and copolymers and blends of poly(p-dioxanone), and poly(trimethylene carbonate).

8. A method of forming a tubular stent in situ in a body lumen, comprising the steps of:

a) inserting into the lumen a composite construct comprising a coil formed by wrapping a strand about an axis, said coil being narrower in diameter than the inside diameter of said lumen, said strand comprising an outside portion and an inside portion of a material different from the outside portion;

b) heating said coil to a temperature sufficient to melt only the outside portion of the strand but not the inside strand portion;

c) expanding the coil while still at said temperature until its diameter approximates that of the lumen; and d) cooling the coil so as to solidify the melted surface portion while the coil is expanded, so that the coil solidifies into a tube.

9. A method as defined in claim 8, wherein said step of heating comprises applying heat from the inside of the coil, outward.

10. A method as defined in claim 8 or 9, wherein said expanding step comprises applying pressure from inside the coil, outward.

* * * * *